(12) United States Patent
Florent et al.

(10) Patent No.: US 8,718,349 B2
(45) Date of Patent: May 6, 2014

(54) LIVE REGISTRATION FOR VESSEL TREATMENT

(75) Inventors: Raoul Florent, Ville d'Avray (FR); Nicolaas Hylke Bakker, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 26 days.

(21) Appl. No.: 13/387,234

(22) PCT Filed: Sep. 22, 2010

(86) PCT No.: PCT/IB2010/054280
§ 371 (c)(1),
(2), (4) Date: Jan. 26, 2012

(87) PCT Pub. No.: WO2011/039681
PCT Pub. Date: Apr. 7, 2011

(65) Prior Publication Data
US 2012/0177277 A1    Jul. 12, 2012

(30) Foreign Application Priority Data

Sep. 29, 2009  (EP) .................................... 09305915

(51) Int. Cl.
*G06K 9/00*    (2006.01)

(52) U.S. Cl.
USPC ......................................................... 382/132

(58) Field of Classification Search
USPC ................................................ 382/130, 132
See application file for complete search history.

(56) References Cited

U.S. PATENT DOCUMENTS

| 4,263,916 A | 4/1981 | Brooks et al. |
| 7,330,576 B2 | 2/2008 | Raman et al. |
| 7,356,367 B2 | 4/2008 | Liang et al. |
| 7,558,611 B2 | 7/2009 | Arnold et al. |
| 2006/0023840 A1 | 2/2006 | Boese |
| 2006/0184006 A1* | 8/2006 | Chen et al. ..................... 600/416 |
| 2008/0298656 A1 | 12/2008 | Yim et al. |
| 2012/0230565 A1* | 9/2012 | Steinberg et al. ............. 382/130 |

FOREIGN PATENT DOCUMENTS

| WO | 2006063141 A2 | 6/2006 |
| WO | 2008050315 A2 | 5/2008 |
| WO | 2009144697 A1 | 12/2009 |

* cited by examiner

*Primary Examiner* — Anand Bhatnagar
*Assistant Examiner* — Soo Park

(57) ABSTRACT

The present invention relates to accurate positioning for vessel intervention procedures, particularly to a method for accurate positioning for vessel intervention procedures, a medical imaging system for accurate positioning for vessel intervention procedures and a catheterization laboratory system for accurate positioning for vessel intervention procedures. First, at least one X-ray image of a vessel region of interest is acquired (24) with injected contrast agent. Further, vessel information data is identified (26) within the at least one acquired image. Then, first calcification features of the vessel in the vessel region of interest in the at least one acquired image are detected (28). Further, vessel representation is generated (30) using the vessel information data and the detected calcification features. Further, at least one current fluoroscopic image of the vessel region of interest is acquired (32). Then, second calcification features of the vessel in the vessel region of interest in the at least one current fluoroscopy image are detected (34), wherein the second calcification features are according to the first calcification features. Further, the vessel representation is registered (36) with the fluoroscopy image, wherein the calcification features are used for the registration. Then, a composite image is generated (38) by combining the vessel representation with the at least one fluoroscopy image. Further, a composite image is displayed (40).

20 Claims, 19 Drawing Sheets

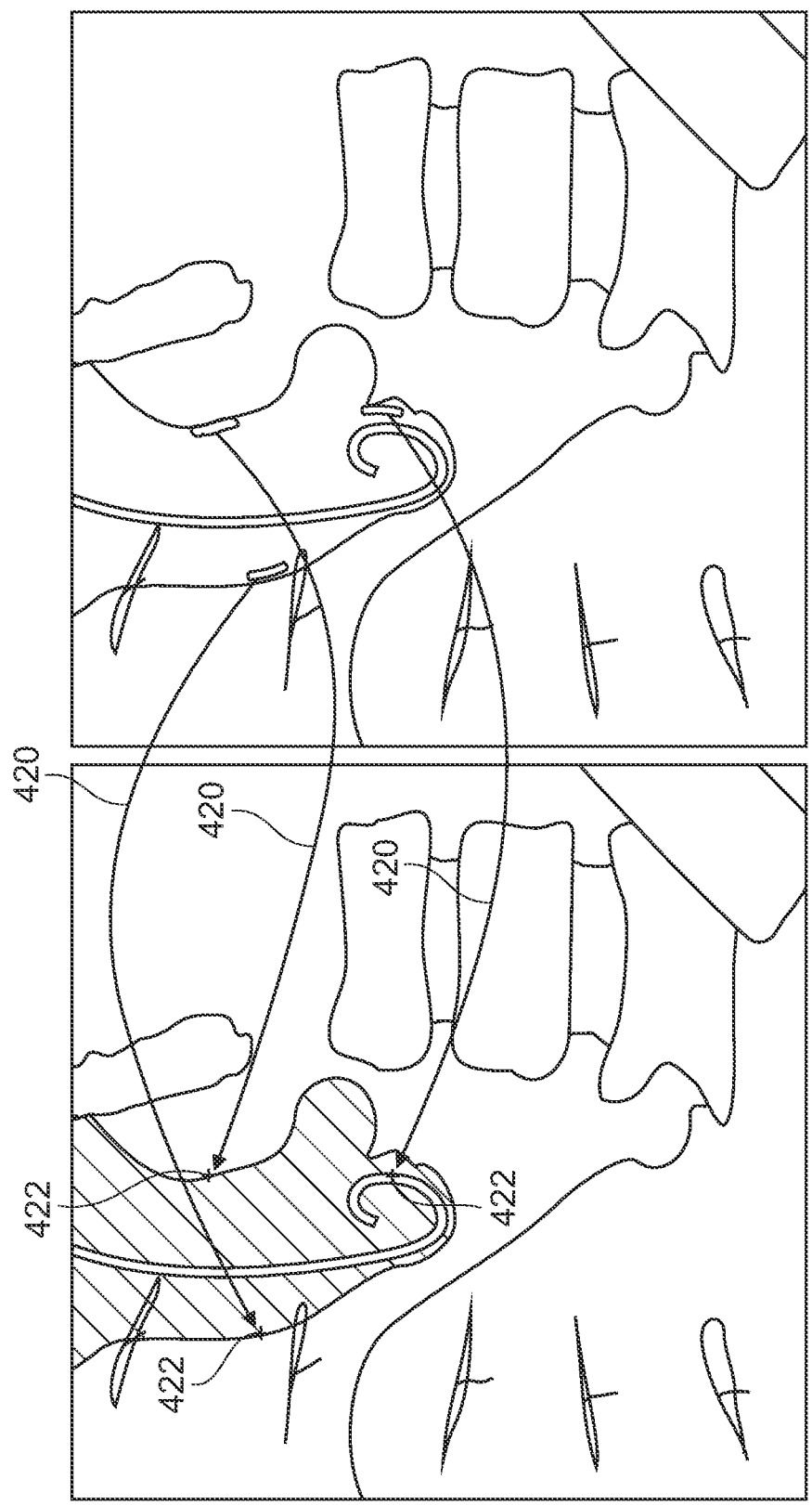

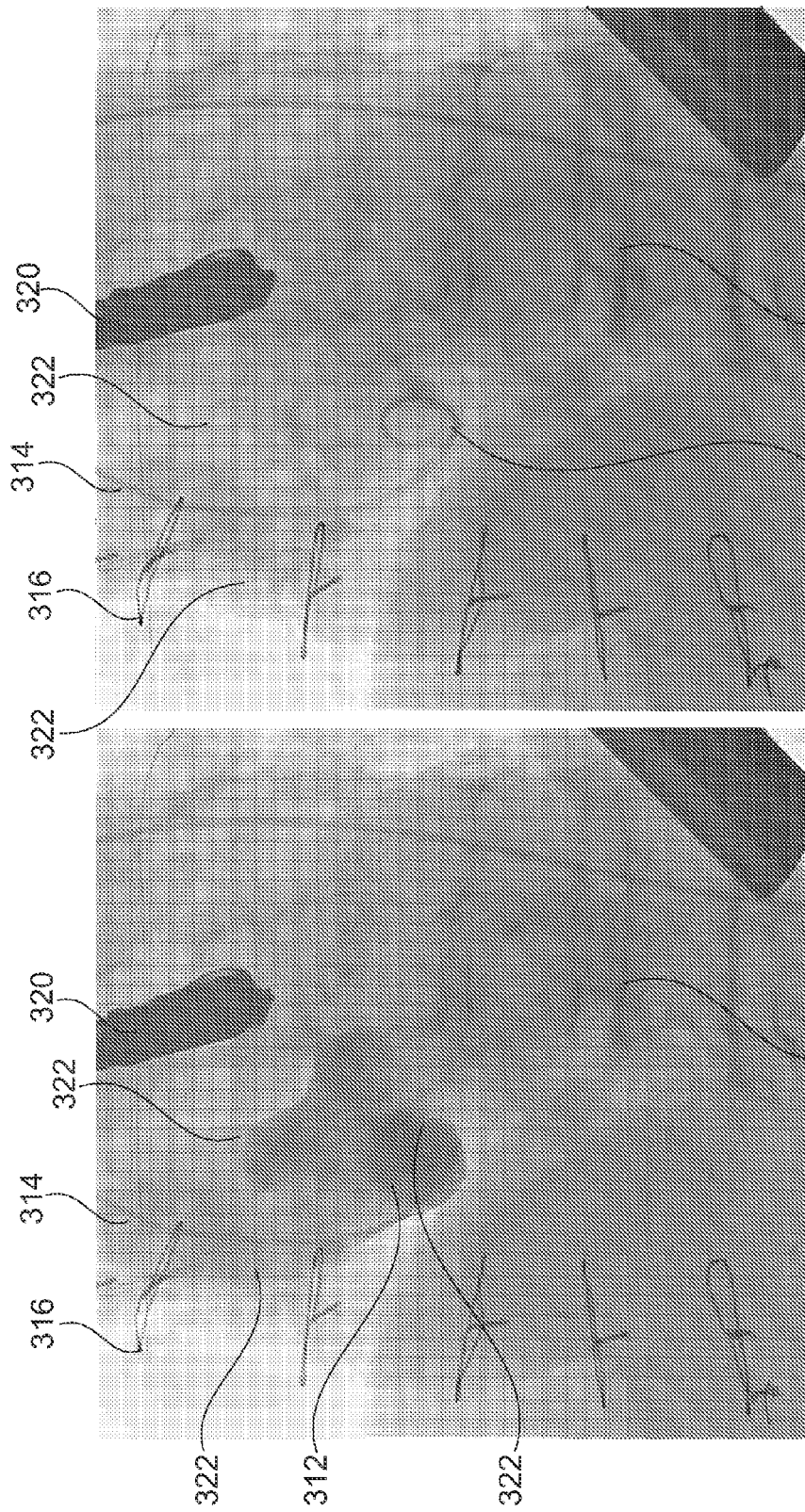

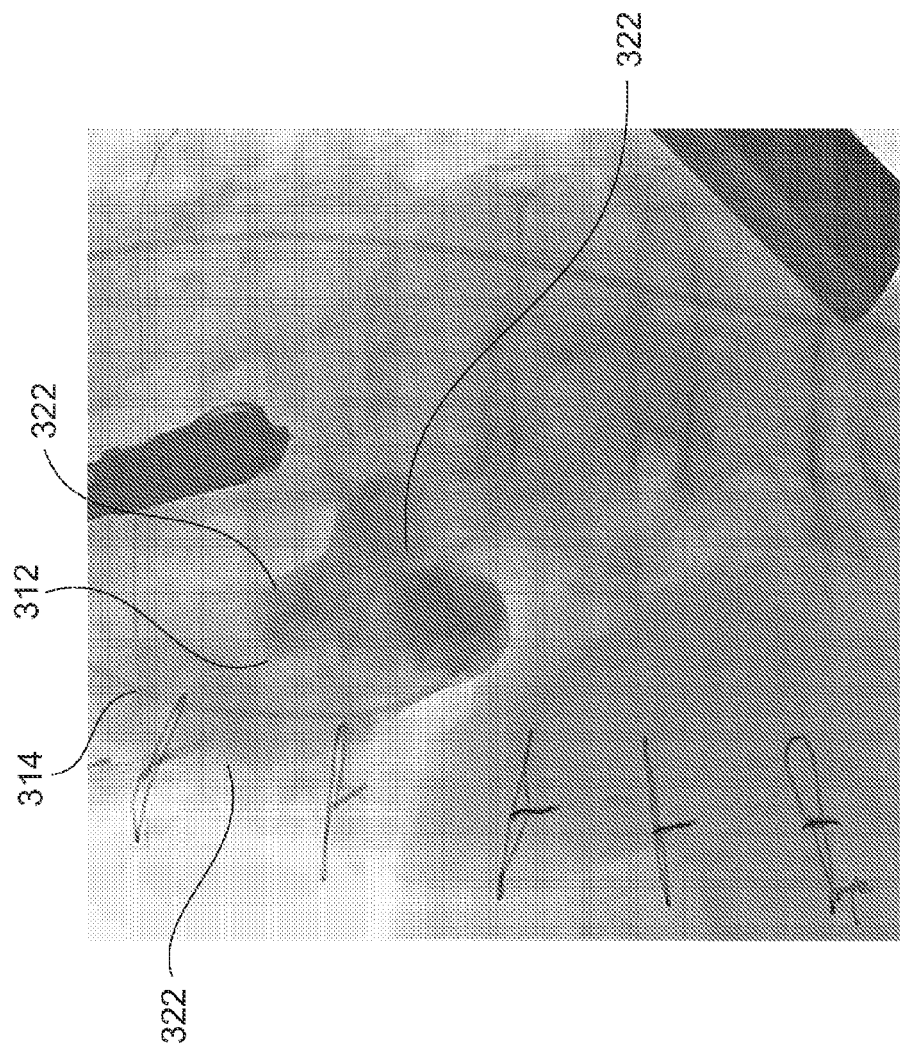

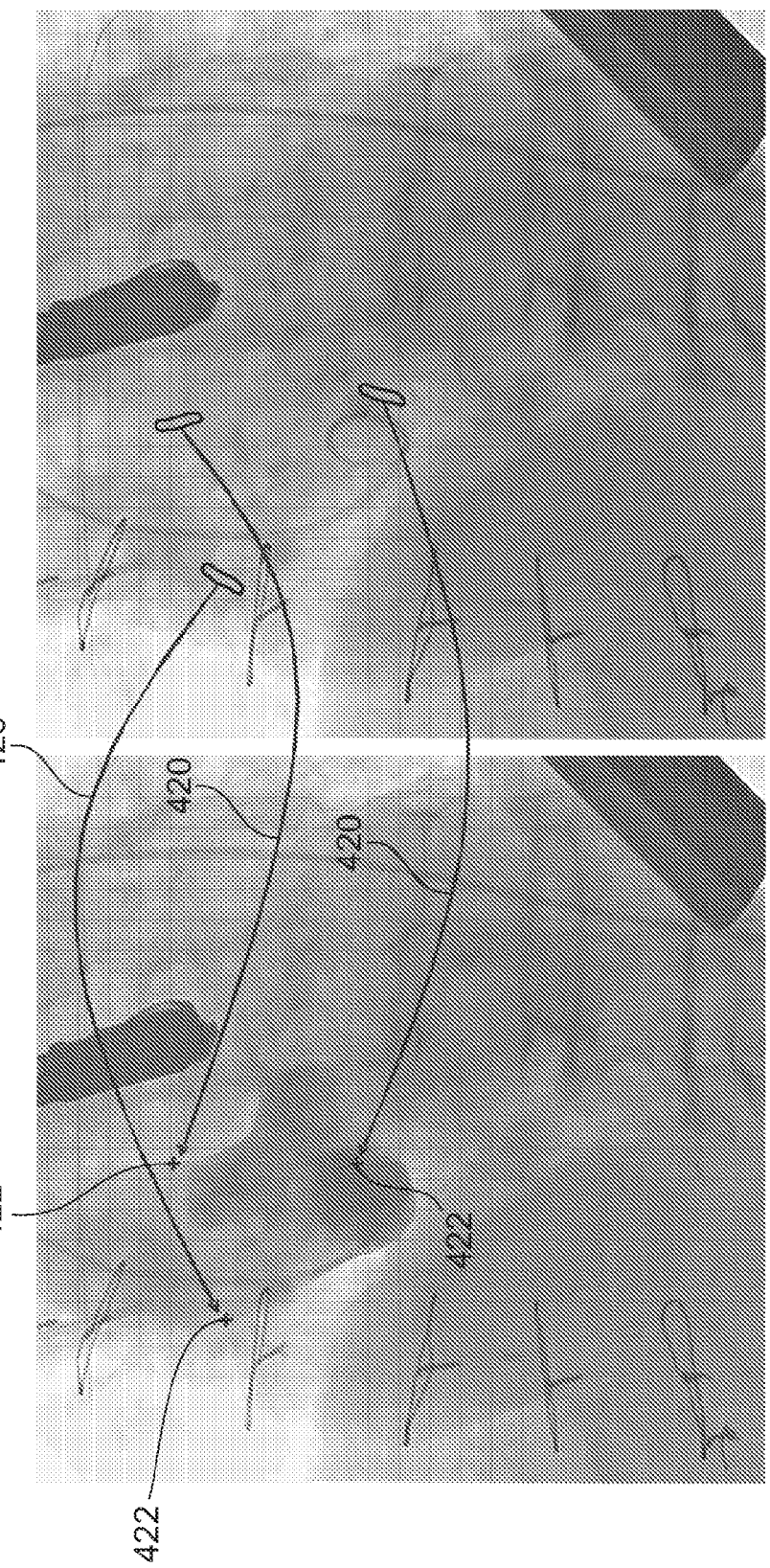

LIVE REGISTRATION FOR VESSEL TREATMENT

FIELD OF THE INVENTION

The present invention relates to accurate positioning for vessel intervention procedures, particularly to a method for accurate positioning for vessel intervention procedures, a medical imaging system for accurate positioning for vessel intervention procedures and a catheterization laboratory system for accurate positioning for vessel intervention procedures.

BACKGROUND OF THE INVENTION

Vessel intervention procedures often comprise the task to position a device inside the vessel prior to further steps. For example, stents may have to be positioned inside the vessel prior to deployment. As another example, in percutaneous aortic valve replacement interventions (PAV replacement), the implantable device, in other words an artificial heart valve replacement, is positioned, for example, under fluoroscopy prior to deployment. In the PAV, to achieve this positioning, a super aortic angiography with contrast agent is performed in order to determine the optimal projection for PAV deployment. For example, a frame is manually selected, stored and subsequently used as pre-implant reference image. But is has been shown that the cardiologist or cardiac surgeon, or in case of other vessel interventions a surgeon or other clinical staff member, constantly has to mentally merge the information from the reference image with fluoro images acquired during the intervention, in other words with the live fluoro images. This mental process is prone to error and makes positioning a delicate and tiring operation. As an additional disadvantage, the breathing and heart beating motions make this mental merging operation more complex. Thus, the manually required reference image is only of certain support, because the cardiologist or cardiac surgeon, for example, has to connect the information from the reference image with fluoro images taking live during the operation procedure using his imagination.

SUMMARY OF THE INVENTION

The present invention aims at providing the cardiologist or surgeon with better information during vessel interventions.

The object may be reached with a medical imaging apparatus for accurate positioning for vessel intervention procedures and a method for accurate positioning for vessel intervention procedures as well as with an X-ray imaging system and a catheterization laboratory system according to the independent claims.

In an exemplary embodiment, a method for accurate positioning for vessel intervention procedures is provided, comprising the following steps. First, at least one X-ray image of a vessel region of interest is acquired with injected contrast agent. Further, vessel information data is identified within the at least one acquired image. Then, first calcification features of the vessel in the vessel region of interest in the at least one acquired image are detected. Further, a vessel representation is generated using the vessel information data and the detected calcification features. Further, at least one current fluoroscopic image of the vessel region of interest is acquired. Then, second calcification features of the vessel in the vessel region of interest in the at least one current fluoroscopy image are detected, wherein the second calcification features are corresponding to the first calcification features. Further, the vessel representation is registered with the fluoroscopy image, wherein the calcification features are used for the registration. Then, a composite image is generated by combining the vessel representation with the at least one fluoroscopy image. Further, a composite image is displayed on a display.

The term "corresponding" means that the features in one of the images are according to the same features in the other one of the images. Simply said, the first and second calcification features are the same calcification features, only in different images. Of course, the terms first and second calcification features can each comprise one or more calcification features.

To base the registration on the detected calcification features provides the advantage that no additional feature, such as an intervention tool, has to be provided for the registration process. Further, the disadvantage of an interventional tool inside larger vessels, used for registration, leading to imprecise or false alignment due to the possible movement of the tool inside the vessel volume is thus prevented.

The method according to the invention provides an image with precise registration without artificial registration landmarks, which result can easily be seen on the image. If the calcification features or spots are masked in the real time images, it is possible to determine if the proposed registration approach is indeed involved.

The term "accurate positioning" refers to features that help accurate positioning, which usually is a local and precise task. But the accurate positioning according to the invention can also be used for device steering, which is usually supported by term roadmapping, which term refers to the super-imposition of a vessel mask over a live non-contrasted image.

According to an exemplary embodiment, the calcification features are determined as landmarks for linking the two images.

According to an exemplary embodiment, the steps of detecting first and second calcification features respectively, comprise localizing the calcification features within the respective image data.

According to an exemplary embodiment, the images can comprise 2D image data as well as 3D image data. In other words, also 3D image data of the vessel region of interest can be registered to 3D image data or 2D image data of a live or current situation.

According to an exemplary embodiment, the 3D comprises pre-/peri-interventional 3D data, such as CT-scanner data, or C-arm-CT data, which data, for example, is used for identifying vessel information data, detecting first calcification features and generating vessel representation acquiring.

In those data, the aortic root, possibly together with calcification features can be segmented or enhanced, and the results of those operations can be used to facilitate the detection/tracking and registration job described above.

According to an exemplary embodiment, the current fluoroscopy image is acquired with a prosthesis inserted into the vessel.

According to an exemplary embodiment, a method is provided with acquiring a sequence of images of the region of interest with injected contrast agent and with selecting the image with the best contrast for the following steps.

According to an exemplary embodiment, a sequence of images is acquired comprising images of a contrast phase and comprising images of a non-contrast phase. The images of the sequence are tracked until the contrast agent starts disappearing. The calcification features are identified once they become visible on the tracked images of the sequence. The spatial relationships linking the contours are recorded during the tracking phase and applied to the calcification features.

According to an exemplary embodiment, a method is provided wherein the spatial relationships linking the contours are applied to the calcification features in a tracking manner.

According to an exemplary embodiment, the sequence of images is acquired comprising images wherein the vessel is filled with injected contrast agent such that the calcification features are not visible and comprising images wherein the vessel is less filled with injected contrast agent such that the calcification features are visible. The images of the sequence are back-tracked until the contrast agent starts disappearing. The calcification features are identified once they become visible on the back-tracked images of the sequence. The spatial relationships linking the contours are recorded during the back-tracking phase and applied to the calcification features in a forward tracking manner.

This provides the detection of the calcification features in the reference image also in those cases where the vessel is substantially filled with contrast agent such that the calcification features are likely to be virtually invisible in the reference image.

According to an exemplary embodiment, a method is provided with estimating the background in the at least one image and subtracting the background from the image by performing a DSA (digital subtraction angiography) before detecting first calcification features.

According to an exemplary embodiment, a method is provided wherein 3D pre-/peri-interventional data is used for the step of identifying vessel information data, the step of detecting first calcification features and the step of generating vessel representation acquiring.

According to an exemplary embodiment, the at least one current fluoroscopy image comprises a sequence of live images.

According to a further exemplary embodiment, the vessel of interest is the aorta.

According to an exemplary embodiment, the angiogram is an aortagram.

According to a further exemplary embodiment, instead of or in addition to an aortagram, a 3D image data volume is used and the aorta is segmented and the calcification features or calcification areas are identified.

According to an exemplary embodiment, the calcification features are calcification spots within the outline of the aorta.

For example, the calcification spots are situated on the aortic root.

According to an exemplary embodiment, the inserted prosthesis is an artificial heart valve device.

According to an exemplary embodiment, the acquisition comprises acquiring 3D images of the aortic root.

For example, 3D images are acquired by CT or C-arm CT such as 3DRX.

According to an exemplary embodiment, a step of generating a composite image comprises a geometrical transformation such to bring the reference image into spatial correspondence with the live image.

According to an exemplary embodiment, 3D data is used. The vessel representation is identified or located on the 3D data. This vessel representation is then registered with an interventional contrast-filled 2D image. Exploitable calcifications are then identified in the 2D images. The calcifications are further linked to the vessels as seen in the 2D contrasted images. Then, the 3D data is registered with the injected 2D image, and since the 2D injected image is linked to the calcification positions, the final 3D-model-to-live-image-registration can be achieved.

However, 3D data has the advantage that it can be used to derive the vessel representation, but is can also be used to help calcifications, vessel candidate selection, vessel candidate detection or vessel candidate tracking.

The object of the invention may also be reached with a medical imaging system for accurate positioning for vessel intervention procedures, comprising at least one X-ray image acquisition device, a data processing unit and a display device. The X-ray image acquisition device is adapted to acquire at least one X-ray image of a vessel region of interest with injected contrast agent and to acquire at least one current fluoroscopy image of the vessel region of interest. A data processing unit is adapted to identify vessel information data within the at least one acquired image. The data processing unit is also adapted to detect first calcification features of the vessel in the vessel region of interest in the at least one acquired image and to generate vessel representation using the vessel information data and the detected calcification features. The data processing unit is also adapted to detect second calcification features of the vessel in the vessel region of interest in the at least one current fluoroscopy image, wherein the second calcification features are corresponding to the first calcification features, and to register the vessel representation with the fluoroscopy image, wherein the calcification features are used for the registration. The data processing unit is also adapted to generate a composite image by combining the vessel representation with the at least one fluoroscopy image. The display device is arranged to display the composite image.

According to an exemplary embodiment, the calcification features are determined as landmarks for linking the two images.

For example, images can comprise 2D image data as well as 3D image data. In other words, also 3D image data of the vessel region of interest can be registered to 3D image data or 2D image data of a live or current situation.

According to an exemplary embodiment, the current fluoroscopy image is acquired with a prosthesis inserted in the vessel.

According to an exemplary embodiment, the X-ray image acquisition device is adapted to acquire a sequence of images of the region of interest with injected contrast agent and the data processing unit is adapted to select the image with the best contrast.

According to an exemplary embodiment, the X-ray image acquisition device is adapted to acquire a sequence of images comprising images of a contrast phase and comprising images of a non-contrasted phase. The data processing unit is adapted to track the images of the sequence until the calcification features are visible in the non-contrasted phase and to locate the calcification features with respect to the vessel information data corresponding to an acquired image in the contrast-phase. The data processing unit is also adapted to record the spatial relationships linking the contours during the tracking phase and to apply the spatial relationships to the calcification features.

According to an exemplary embodiment, the data processing unit is also adapted to apply the spatial relationships to the calcification features in a tracking manner.

According to an exemplary embodiment, the X-ray image acquisition device is adapted to acquire a sequence of images comprising images wherein the vessel is filled with injected contrast agent such that the calcification features are not visible, and comprising images wherein the vessel is less filled with injected contrast agents such that the calcification features are visible. The data processing unit is adapted to track the images of the sequence until the contrast agent starts to disappear and to identify the calcification features once they become visible on the tracked images of the sequence.

The data processing unit is adapted to record the spatial relationships linking the contours during the back-tracking phase and to apply the spatial relationships to the calcification features in a forward tracking manner.

According to an exemplary embodiment, the data processing unit is adapted to estimate the background in the at least one image and to subtract background from the image by performing a digital subtraction angiography (DSA) before detecting first calcification features.

According to an exemplary embodiment, the X-ray image acquisition device is adapted to acquire a sequence of live images.

According to an exemplary embodiment, the vessel of interest is the aorta.

According to an exemplary embodiment, the data processing unit is adapted to acquire an aortagram as an angiogram.

According to an exemplary embodiment, the data processing unit is adapted to detect calcification spots on the outline of the aorta representing the calcification features.

For example, the calcification spots are situated on the aortic root.

According to an exemplary embodiment, the inserted prosthesis is an artificial heart valve device.

According to an exemplary embodiment, the at least one X-ray image acquisition device is adapted to acquire 3D images of the aortic root.

For example, 3D images are acquired by CT or 3DRX, for example of vessels such as the aorta.

According to an exemplary embodiment, the data processing unit is adapted to generate a composite image by a geometrical transformation performed such to bring the reference image into spatial correspondence with the live image.

For example, the geometrical transform is applied to overlay a synthetic vessel representation or model to the live image.

The object may also be reached with an X-ray imaging system with an arrangement according to one of the preceding embodiments.

The object may also be reached with a catheterization laboratory system with an arrangement according to one of the afore-mentioned embodiments.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

However, the computer program may also be presented over a network like the World Wide Web and can be down loaded into the working memory of a data processor from such a network. According to a further exemplary embodiment of the present invention, a medium for making a computer program element available for down loading is provided, which computer program element is arranged to perform a method according to one of the previously described embodiments of the invention.

It must be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

BRIEF DESCRIPTION OF THE DRAWINGS

The aspect defined above and further aspects, features and advantages of the present invention can also be derived from the examples of embodiments to be described herein after and are explained with reference to examples of embodiments, but to which the invention is not limited. The invention will be described in more detail hereinafter with reference to the drawings.

FIGS. 11 and 12 show an exemplary embodiment of tracking of calcifications from non-injected images to injected images;

FIGS. 16 to 18 show photographic images of the drawings in FIGS. 6 to 8; and

FIGS. 19 to 25 show photographic images of the drawings in FIGS. 9 to 15.

DETAILED DESCRIPTION OF EMBODIMENTS

Figure 1:
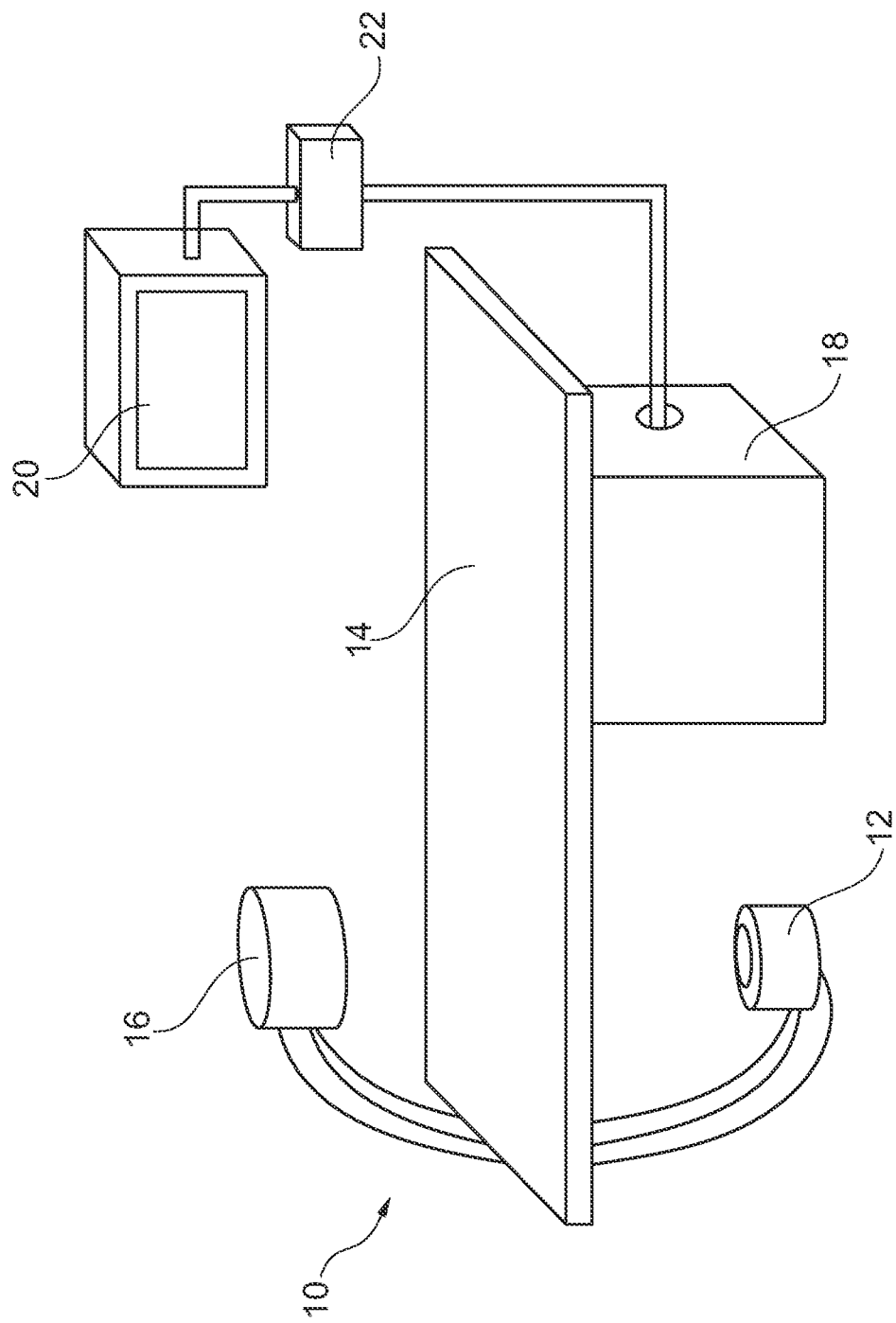
FIG. 1 shows an X-ray imaging system for the use in a catheterization laboratory, for accurate positioning for vessel intervention procedures.

FIG. 1 schematically shows an X-ray imaging system 10 for the use in a catheterization laboratory with an examination apparatus for accurate positioning for heart valve replacement. The examination apparatus comprises an X-ray image acquisition device with a source of X-ray radiation 12 provided to generate X-ray radiation. A table 14 is provided to receive a subject to be examined. Further, an X-ray image detection module 16 is located opposite the source of X-ray radiation 12, i.e. during the radiation procedure the subject is located between the source of X-ray radiation 12 and the detection module 16. The latter is sending data to a data processing unit or calculation 18, which is connected to both the detection module 16 and the radiation source 12. The calculation unit 18 is located underneath the table 14 to save space within the catheterization laboratory. Of course, it could also be located at a different place, such as a different room. Furthermore a display device 20 is arranged in the vicinity of the table 14 to display information to the person operating the X-ray imaging system, i.e. a clinician such as a cardiologist or cardiac surgeon. Preferably the display device 20 is movably mounted to allow for an individual adjustment depending on the examination situation. Also, an interface unit 22 is arranged to input information by the user. Basically, the image detection module 16 generates images by exposing the subject to X-ray radiation, wherein said images are further processed in the data processing unit 18. It is noted that the example shown is of a so-called C-type X-ray image acquisition device. Of course, the invention also relates to other types of X-ray image acquisition devices. The procedure according to the invention is described in more detail below.

Figure 2:
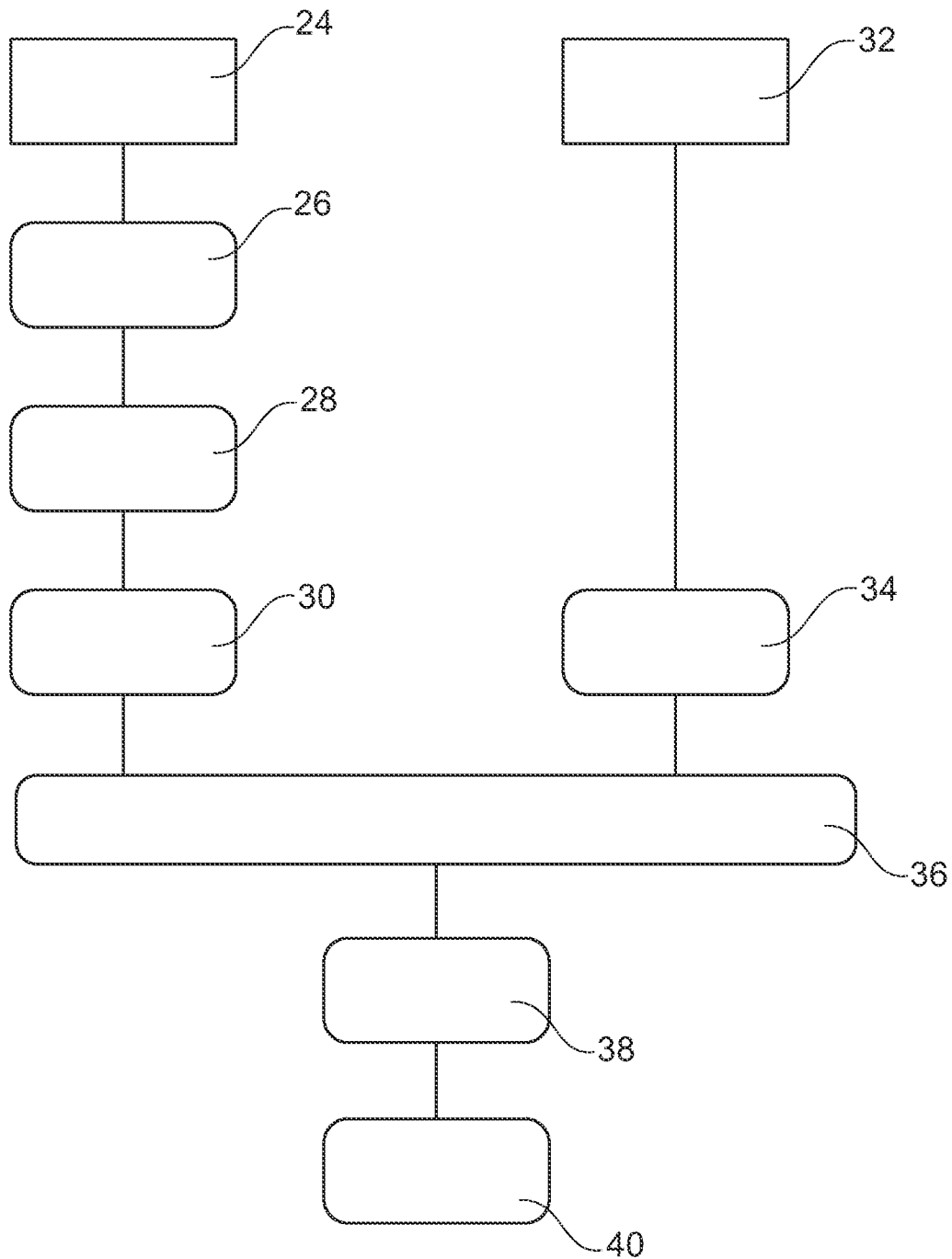
FIG. 2 schematically describes the method steps according to the invention.

FIG. 2 schematically shows a flow chart of the steps according to the invention. In a first acquisition step 24, at least one X-ray image of a vessel region of interest is acquired with injected contrast agent. In an identification step 26, vessel information data is identified within the at least one acquired image. In a first detecting step 28, first calcification features of the vessel in the vessel region of interest are detected in the at least one acquired image. Further, in a generating step 30, a vessel representation is generated using the vessel information data and the detected calcification features. Further, in a second acquisition step 32, at least one current fluoroscopy image is acquired of the vessel region of interest. Then, in a second detection step 34, second calcification features of the vessel are detected in the vessel region of interest in the at least one current fluoroscopy image, wherein the second calcification features are corresponding to the first calcification features.

In other words, the first and second calcification features are the same calcification features, only in different images. Of course, the terms first and second calcification features can each comprise one or more calcification features.

In a registration step 36, the vessel representation is registered with the fluoroscopy image, wherein the calcification features are used for the registration step 36. Further, in a generating step 38, a composite image is generated by combining the vessel representation with the at least one fluoroscopy image. Then, in a display step 40, a composite image is displayed on a display, for example the display 20.

According to an exemplary embodiment, the vessel representation is a generated model of the vessel.

According to an exemplary embodiment, in the case of PAV, the model can also be constituted by a simplified representation containing for instance the projection in the image plane of the valve leaflet plane, and for instance the projection (in the image plane) of the medial axis of the valve.

Generally, the vessel representation must be sufficiently informative for the proper placement of the device, and it must be sufficiently simple enough so as to avoid cluttering the combined image with too much information, and to avoid confusing the interventionalist.

In the PAV case, the prosthesis angle and insertion extent should be accurately controlled. The angle can be controlled by orientating the rotation axis of the prosthesis parallel to the valve medial axis. The insertion extent can be controlled by positioning the valve mid-point with respect to the leaflet plane.

According to an exemplary embodiment, the first acquisition step 24 comprises acquiring a sequence of images of the region of interest with injected contrast agent and selecting the image with the best contrast for the following steps, which embodiment is not further shown in FIG. 2.

Figure 3:
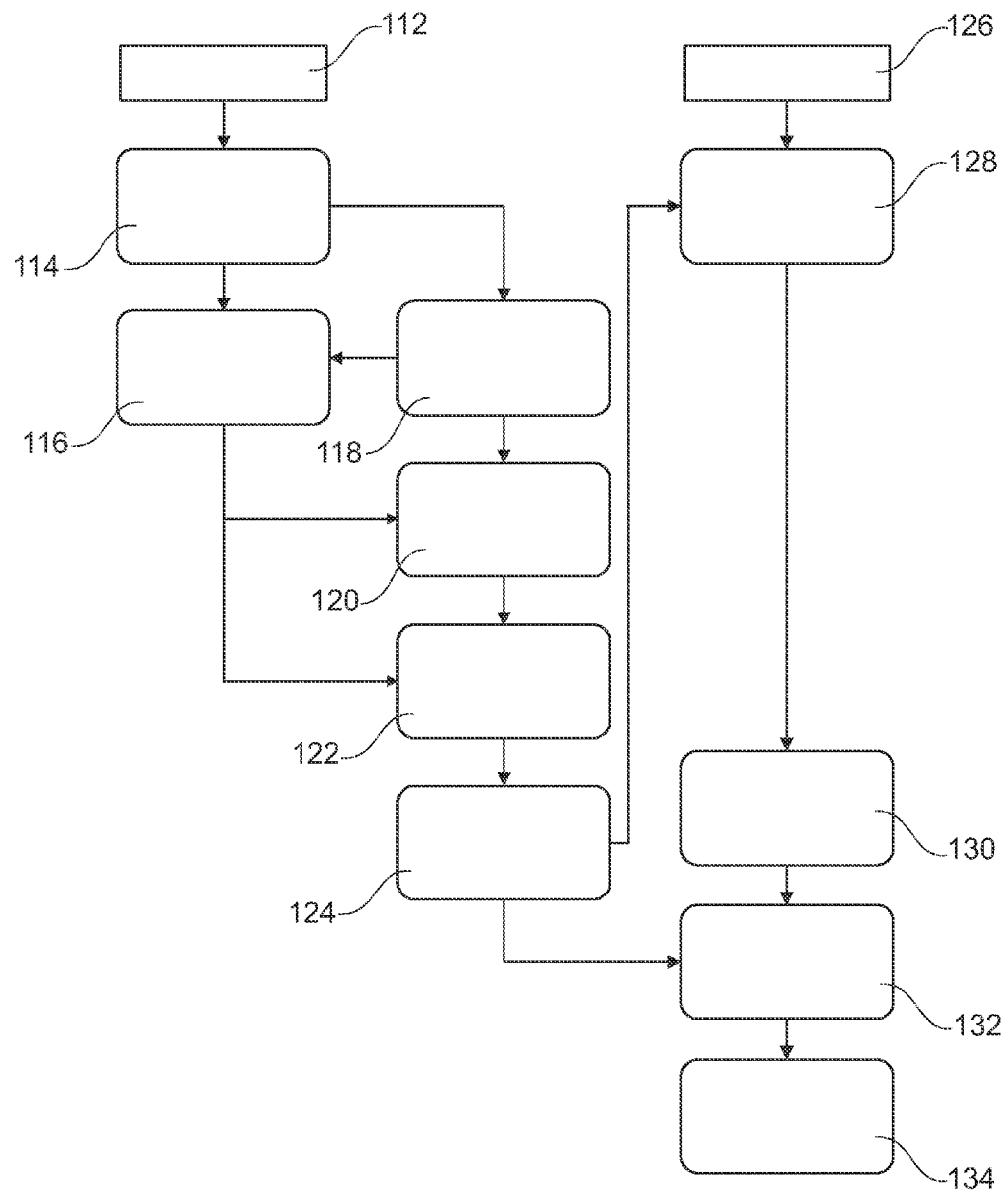
FIG. 3 schematically shows another embodiment of the method of FIG. 2.

According to an exemplary embodiment, shown in FIG. 3, a sequence of images is acquired comprising images wherein the vessel is filled with injected contrast agent, possibly making the calcification features invisible and comprising images wherein the vessel is less filled with injected contrast agent such that the calcification features are visible. This process is also referred to as aortography 112. Further, in a detecting step 114, a certain number of aortic root candidate contours or selection contours, in the reference image are detected at a time $t_0$. Preferably, candidates or selections are used which make this step not too demanding. When 3D data are involved, they can be used to candidate finding.

In a further tracking step 116, of the candidate contour, the images of the sequence are tracked until the contrast agent starts disappearing.

This tracking can occur causally (that is along increasing image time instants), or anti-causally (that is along decreasing time instant).

This occurs at a point of time on the time track, which time is referred to as $t_1$. All the spatial relationships linking the contours during the tracking phase are recorded (not further shown in FIG. 3).

Further, a determination step 118 is performed for contrast agent fading instant at time $t_1$ by monitoring of the contrast agent amount along the temporal axis, for instance using filtering and histogram techniques.

Further, in an identification step 120, at time $t_1$, calcification candidate spots, or in other words calcification features, close to the candidate contours are identified and seemingly animated with a similar motion. Of course, this motion can, for example, include vibration, such as in hyper-pacing cases. It must be noted that at time $t_1$ the calcification spots start to be visible while the candidate contours are still trackable down to that frame.

Further, in a reverse tracking step 122, the spatial relationships linking the contours are applied to the calcification features, for example in a forward tracking manner.

The reason for this shall be described in the following: Because the contours have been tracked from $t_0$ to $t_1$ and because the calcification candidate spots in time $t_1$ can be localized with respect to the $t_1$ candidate contours, it is possible to determine the spatial relationships between the visible candidates at $t_1$ and their hidden counterparts at $t_0$, for which the term reverse tracking is used. However, this enables the definition of a set of landmarks $S_A(t_0)$ for the reference aortagram at time $t_0$.

Thus, after the reverse tracking step 122, in a determining step 124, the landmarks $S_A(t_0)$ are determined. According to the invention, the same kind of steps described above, can be reproduced in the fluoro live images, for example.

According to the exemplary embodiment shown in FIG. 3, at least one current fluoroscopy image of the vessel region of interest is acquired in an acquisition step 126. Further, in an identification step 128, calcification features or calcification candidate spots are identified at time t, for example in case of a sequence of fluoro images, along the fluoro sequence. In addition to the search of the landmarks $S_A$, which criteria involves contrast agent as an aspect, the shape and the motion of those spots are likely to be involved. Once the calcification spots are identified, in a further identification step 130, a set of landmarks $S_F(t)$ for each fluoro image at the time t can be identified.

Once the landmarks $S_A(t_0)$ and the landmarks $S_F(t)$ are determined in step 124 and 130 respectively, it is possible to register the acquired images of the image acquisition step 112 with the fluoro images acquired in acquisition step 126, for example, during an intervention procedure.

In order to provide an improved image, in a registration step 132, a defined geometrical transformation $G(t_0, t)$ can be used to bring the reference image into spatial correspondence with the live image at time point t, making all sorts of overlay and/or accurate localization scheme possible. The registered and geometrically transformed image data can then be combined and displayed in a further step 130.

According to the invention, the image acquisition device shown in FIG. 1 is adapted to acquire at least one X-ray image of a vessel region of interest with injected contrast agent and to acquire at least one current fluoroscopy image of the vessel region of interest. The data processing unit 18 is adapted to identify vessel information data within the at least one acquired image, to detect first calcification features of the vessel region of interest in the at least acquired image and to generate a vessel representation using the vessel information data and the detected calcification features. The data processing unit 18 is also adapted to detect second calcification features of the vessel in the vascular region of interest in the at least one current fluoroscopy image, wherein the second calcification features are according to the first calcification features. The data processing unit 18 is also adapted to register the vessel representation with the fluoroscopy image, wherein the calcification features are used for the registration, and to generate a composite image by combining the vessel representation with the at least one fluoroscopy image. The display device 20 is arranged to display the composite image.

As an example, the vessel of interest is the aorta. Since treatment of heart valve problems or heart valve diseases becomes more important, because of an aging population, wherein such diseases usually require the replacement of a native heart valve, the invention provides a cardiologist or surgeon with better information, for example, during percutaneous heart valve implantation. Although the invention is exemplarily described in relation with the replacement of the aortic valve, the invention is also focused on the replacement of other types of heart valves, such as pulmonary, mitral and tricuspid valves. Of course, the invention is also focused on other vessel treatments, for example inserting a stent, for example, in vessel region with a defected vessel cross section.

Figure 6:
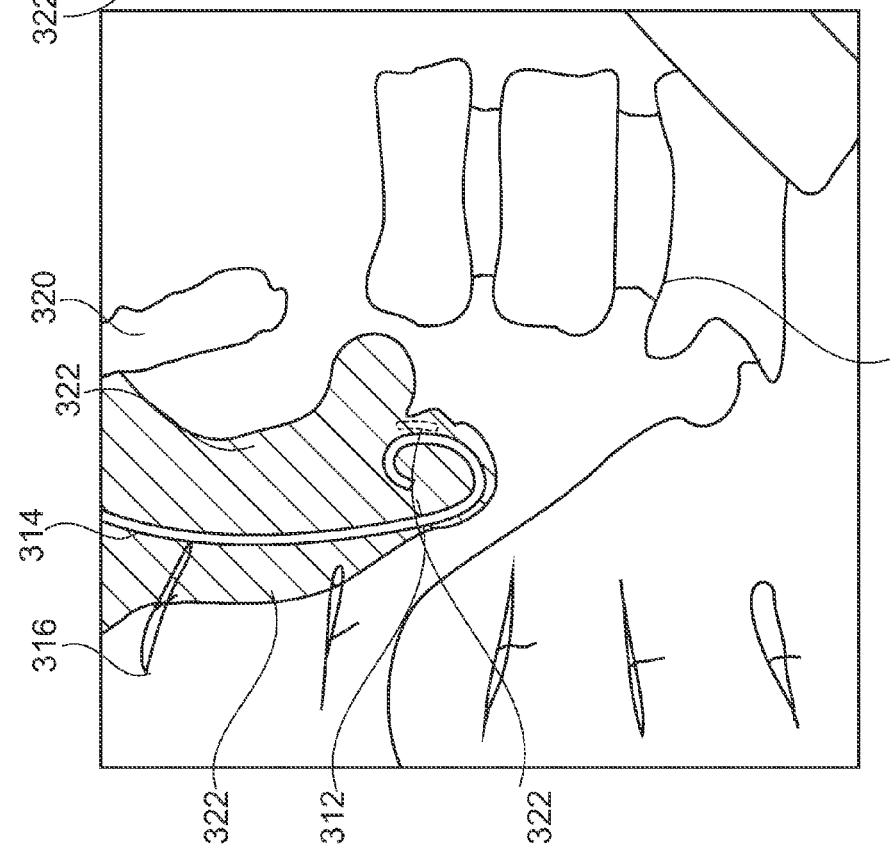
FIG. 6 schematically shows an injected image according to the invention.

In FIG. 6, a heart 210 is shown with a right part 212 and a left part 214 in relation to the main vessels. The right part 212 is placed on the vena cava in the diagram. It should designate the part of the heart irrigated by the right coronary. On top of the left part, an ascending aorta 216 can be seen forming an arch 218 where several other vessels 220 are connected to the aorta 216. The aorta 216 then leads downwards where several further vessels are connected, such as the celiac artery 222 and the superior mesenteric artery. Still further, the aorta splits up into the renal arteries 226 and the inferior mesenteric artery 228 that leads to the iliac arteries 230. This part is also called the abdominal aorta. The connection point to the heart itself, so to speak the starting point of the aorta 216 is the root 232 or aortic root. Further, two coronary arteries 233 are connected in the root region 230. An aortic heart valve which is not shown in FIG. 6 is located at the root 232.

Figure 5:
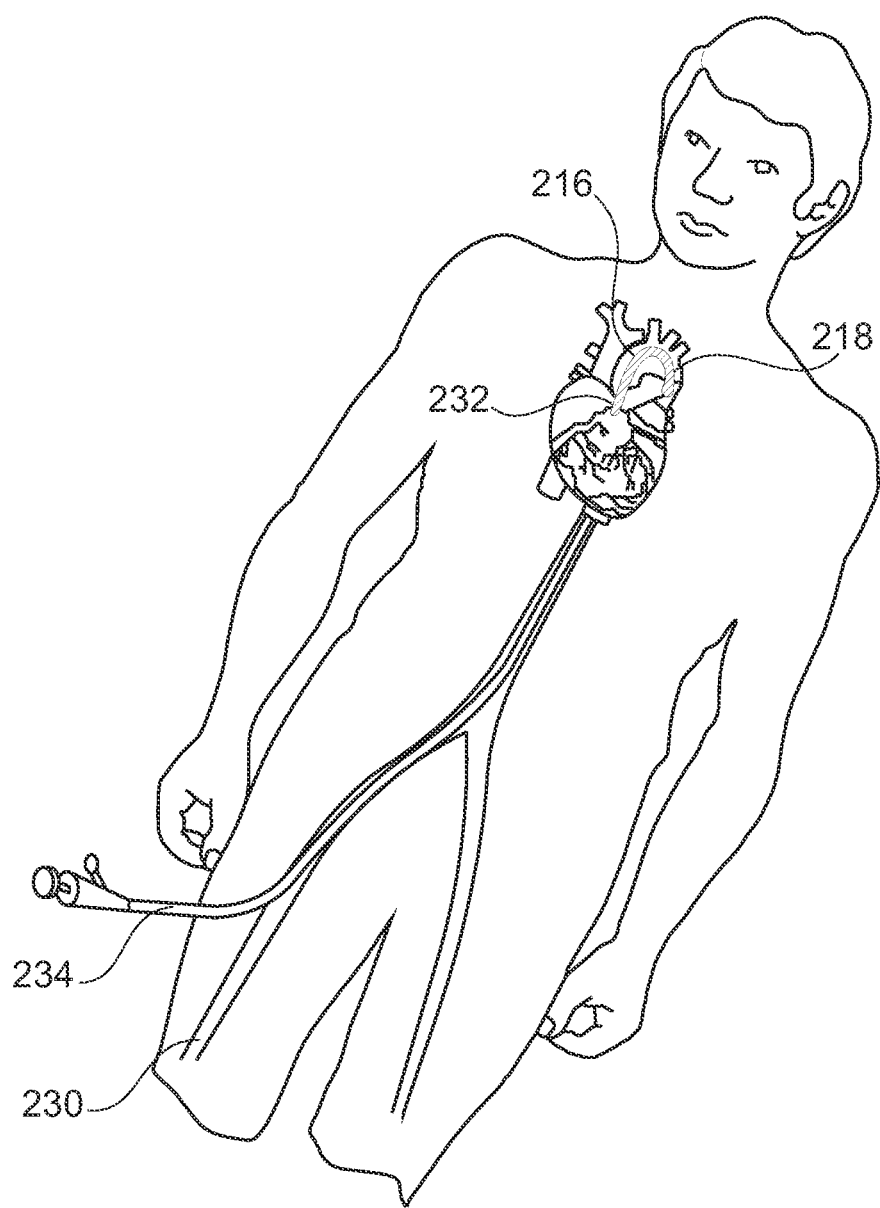
FIG. 5 schematically shows a catheterization of an object as an example for a vessel treatment.

For a heart valve replacement such as the replacement of the aorta valve, located at the root 232, in FIG. 5, a valve delivery catheter 234 is inserted in the groin into one of the iliac arteries 230 and threaded up to the heart valve to be replaced. In other words, the catheter 234 follows the aorta passing the arch 218 until it reaches the root region where the valve is deployed after correct positioning.

Figure 4:
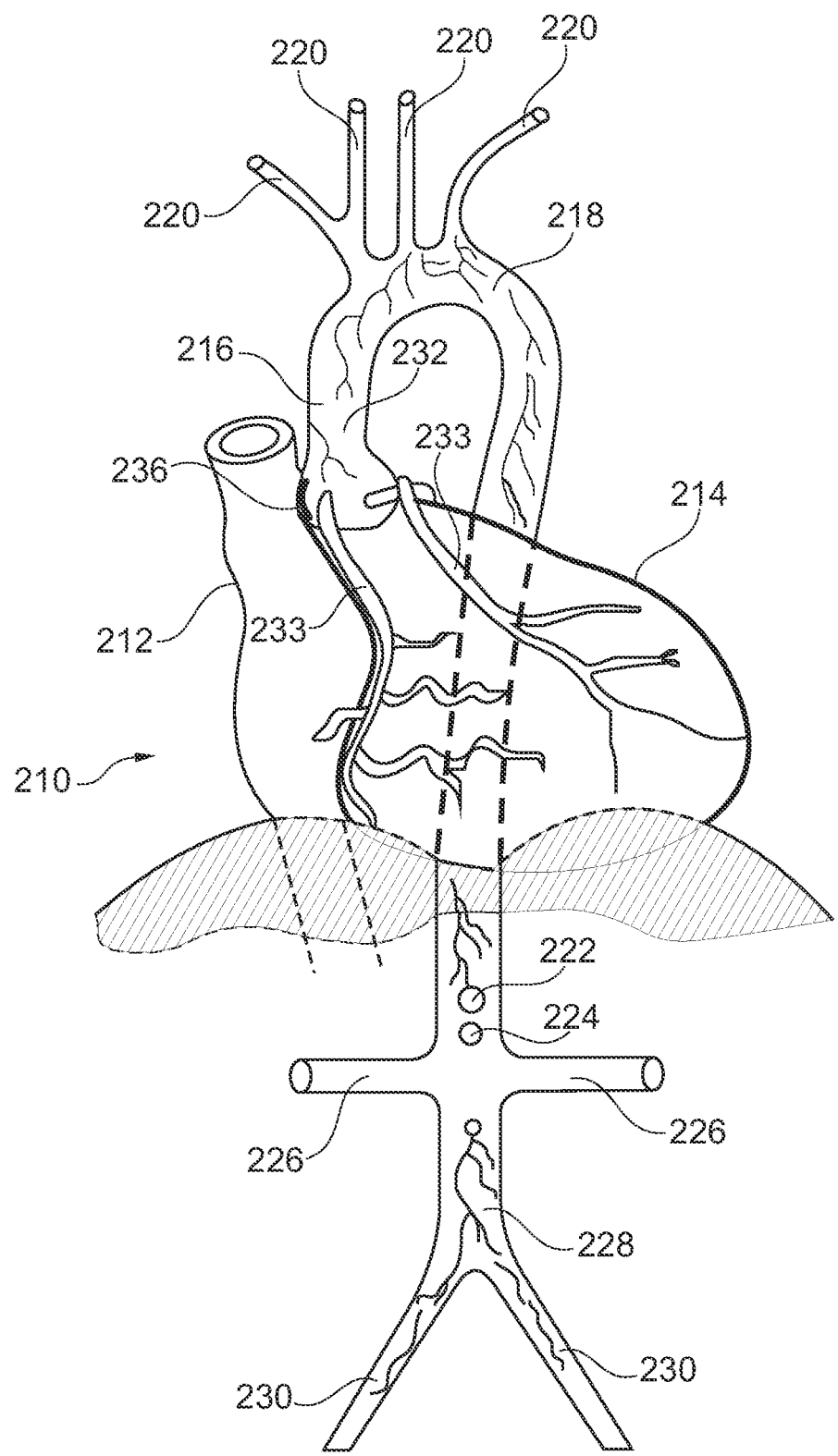
FIG. 4 schematically shows the structure of the aorta.

By providing the surgeon with displaying a composite image, generated according to the method steps described above, the surgeon is provided with improved or enhanced information about the localization or positioning respectively of the catheter or another positioning tool for bringing the artificial heart valve into the correct position. By using calcification spots 236, only schematically indicated in FIG. 4, as registration features, it is possible to combine the vessel representation with a currently acquired image, for example a fluoroscopy image. The vessel representation, for example an aortagram, provides a sort of roadmap to the surgeon, whereas the fluoroscopy image provides the information necessary for the localization of the catheter 234 or other intervention tools. Thus, the displayed composite image provide the cardiac surgeon or cardiologist with the information needed for a correct deployment of the artificial valve. For actual, respectively current, information it is possible to repeat the fluoroscopy image acquisition in a predetermined interval. Usually, the fluoroscopy acquisition step is undertaken without the use of contrast agent. By providing the surgeon with the composite image according to the invention, it is possible, to reduce the amount of contrast agent used during the procedure which means a great relief for patients who have liver problems, for example.

Of course, it is also possible to repeat the angiogram or aortagram acquisition and the following steps for generating or modeling a vessel representation or an aortic root representation at a predetermined rate or according to the actual need, for example, in case a procedure takes longer than actually expected.

According to an exemplary embodiment, the step of generating vessel representation using the vessel information data and the detected calcification features comprising modeling vessel representation using the vessel information data and the detected calcification features.

As an example, FIG. 6 shows an injected image used for an aortagram. Due to the use of contrast agent, an aortic root 312 is visible near the center of the image. Further, an injection catheter 314 can be seen by which the contrast agent is injected in the region of interest. Further, other features such as sternal clips 316, spine elements 318 or an ultrasound probe 320 are also visible within the injected image in FIG. 6.

It must be noted that the injected image of FIG. 6 can be one image out of a sequence of several images of a full aortography sequence, for example. As FIG. 6 shows the aortic root with a substantially filled state that is substantially filled with contrast agent, calcification spots 322 are nearly invisible in the image shown in FIG. 6. Nevertheless, the calcification features 322 are visible in images where the contrast agent starts to disappear (not shown).

These calcification features 322 are detected, which can be performed manually or automatically. Since during the backtracking the detected aortic root contours, visible in FIG. 6, the spatial relationships linking the contours during the backtracking phase are recorded, the calcification features 322 are also known with respect to their spatial relationships. In other words, even if calcification features 322 are not visible at all images of the sequence, it is still possible to know the exact location of the calcification features 322 because the calcification features 322 have a fixed relation to the aortic root contour visible in those images where the calcification features 322 are most often not visible. Whereas, for example the catheter tip or biopsy needle, or other devices, the positioning of the device within a vessel changes constantly and thus would provide only a rough information of the position and not the required preciseness.

Figure 7:
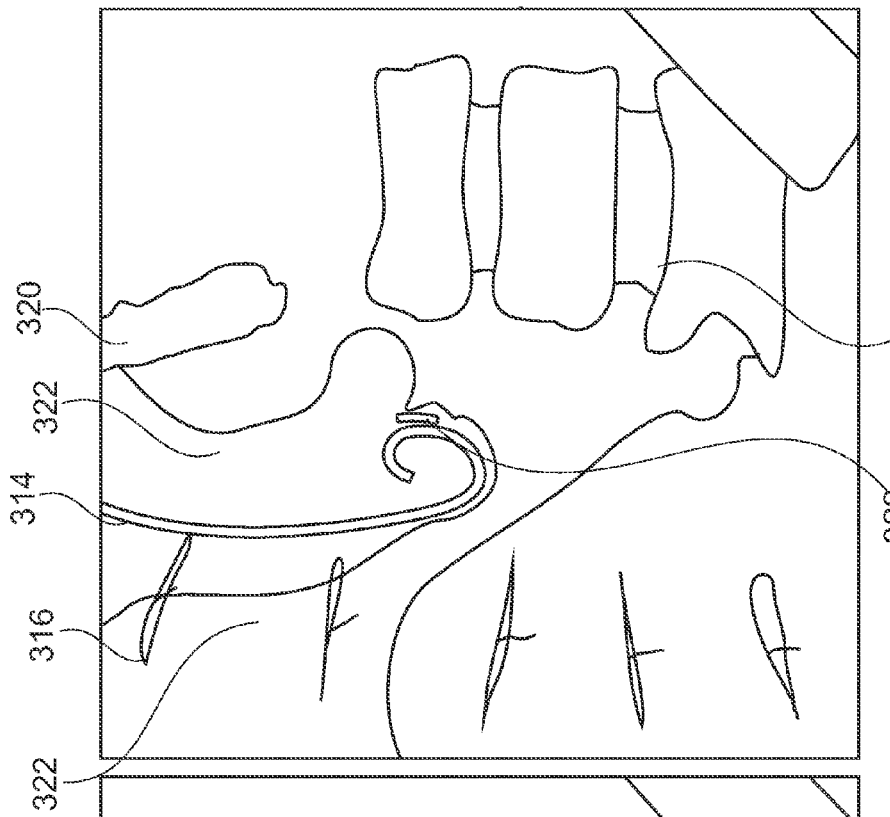
FIG. 7 schematically shows a fluoroscopy image according to the invention.

During the actual intervention procedure, non-injected images are acquired, for example under fluoroscopy, an example of which is shown in FIG. 7. Here, besides the additional features such as sternal clips 316, the spine 318 or the ultrasound probe 320, also the catheter 314 is shown, but the positioning of the catheter can have changed in the meantime.

Figure 8:
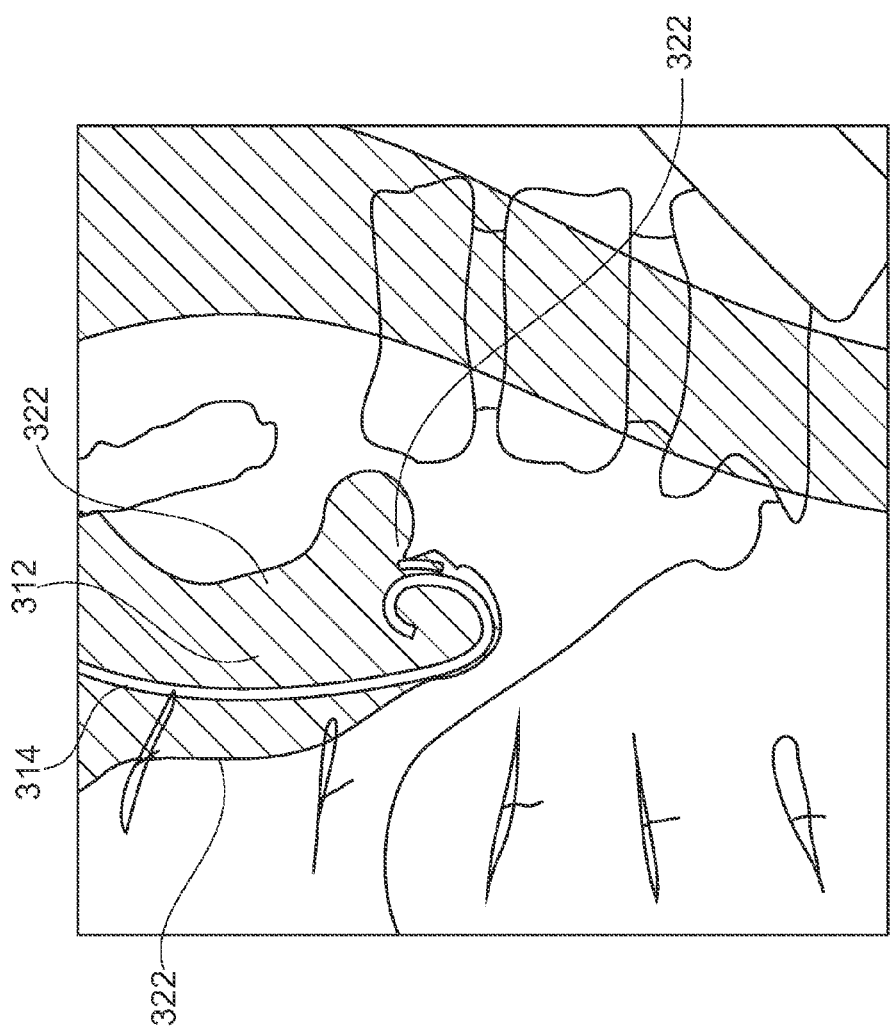
FIG. 8 schematically shows a composite image according to the invention.

In order to combine the information of the aortagram shown in FIG. 6, and the current information provided in the fluoroscopy shown in FIG. 7, the aortic calcification features 322 are detected in the image of FIG. 7 and used for a registration process in order to be able to combine or to generate a composite image, an example of which is shown in FIG. 8. It is noted that the combined image in FIG. 6 comprises a further enhanced image of the image data shown in FIG. 6, also known as an angiogram that is an image where the background has been subtracted in order to clearly visualize only the vessel information.

The method according to the invention provides an image with precise registration without artificial registration landmarks, which result can easily be seen on the image. If the calcification features or spots are masked in the real time images, it is possible to determine if the proposed registration approach is indeed involved.

Figure 10:
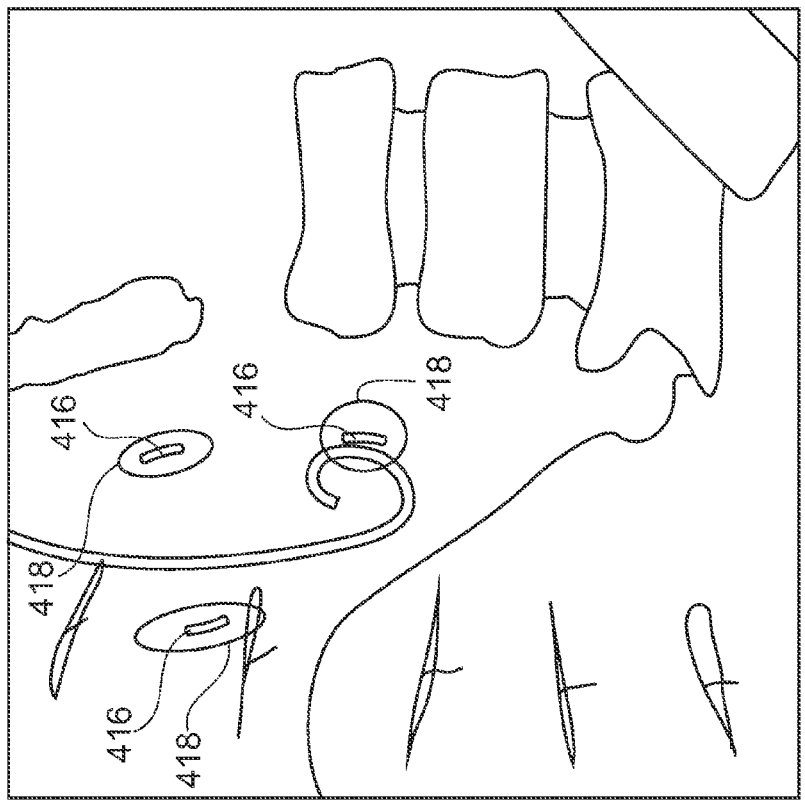
FIG. 10 schematically shows a non-injected image in an aortagram
Figure 9:
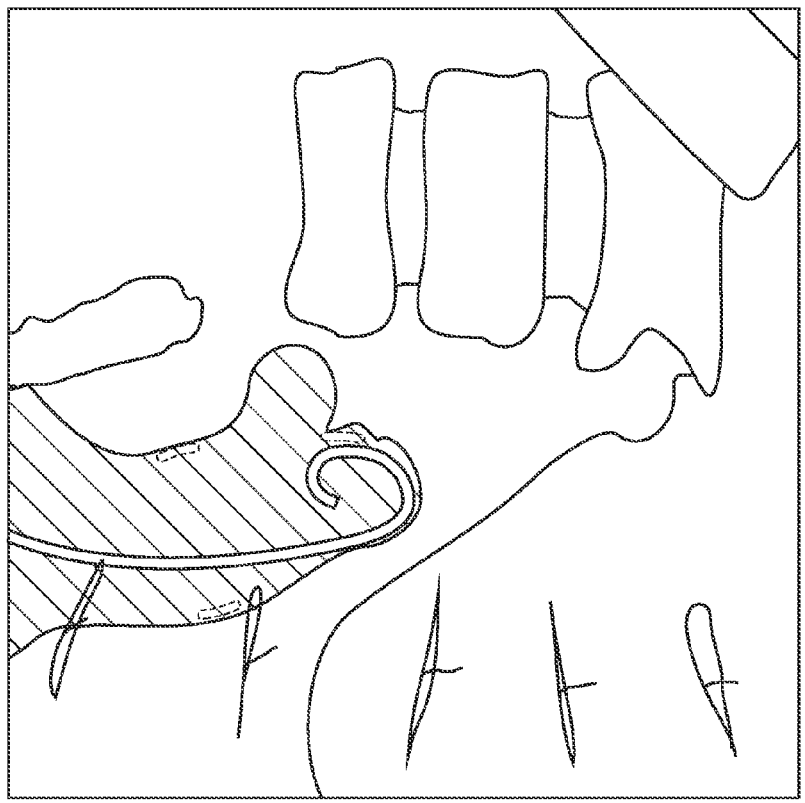
FIG. 9 schematically shows an injected image in an aortagram.

In addition, an exemplary embodiment for accurate positioning is now described with reference to FIGS. 9 to 15. As mentioned above, first, a series of images is acquired during an injection period, comprising an injected image, which leads, for example, to an injected image 412 in an aortagram as shown in FIG. 9. The series of images also comprises non-injected images in an aortagram, an example of a non-injected image 414 is shown in FIG. 10.

The non-injected image is used for identifying calcifications 416, which are indicated with a circle 418 for easier understanding. The calcifications 416, or calcification features, are, for example, aortic calcifications.

Next, the calcifications 416 are tracked from the non-injected images to injected images, which is schematically shown in FIGS. 11 and 12. The tracking is indicated with arrows 420 leading to the respective positions in the image of FIG. 11, which positions are each indicated with a cross 422.

This might also be based on or supported by calcifications detected in 3D pre-interventional steps.

Figure 13:
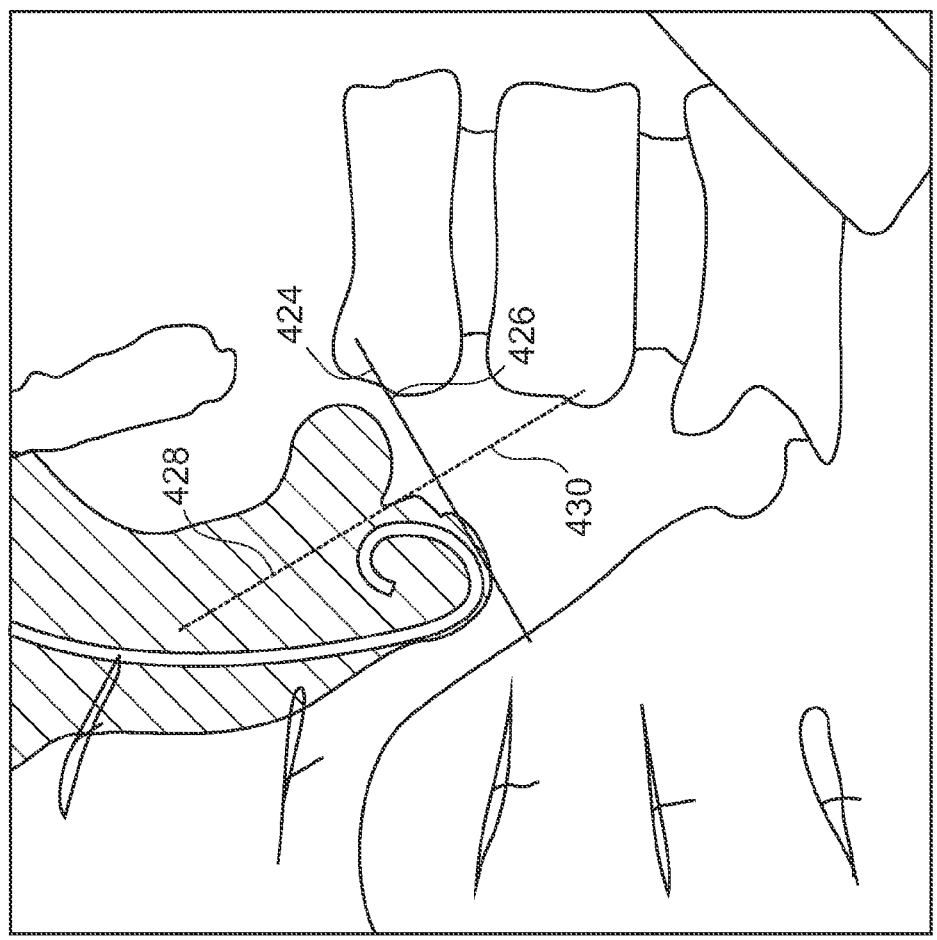
FIG. 13 shows the identification of an aortic valve plane and a medial axis.

Further, as shown in FIG. 13, an aortic valve plane 424, indicated with a straight line 426, and a medial axis 428, indicated with a dotted line 430, are identified. This can be achieved either directly from 2D data or from pre-/peri-interventional 3D data. In the latter case, the aortic valve plane and the medial axis are first determined in 3D through either manual or automatic means, the 3D data set is also registered with the 2D aortagram of FIG. 13 based on the aortic root features present in 3D and 2D, and finally, the registered 3D aortic valve plane and medial axis are projected into the 2D aortagram, thus creating the 2D valve plane 424 and medial axis 428.

Figure 14:
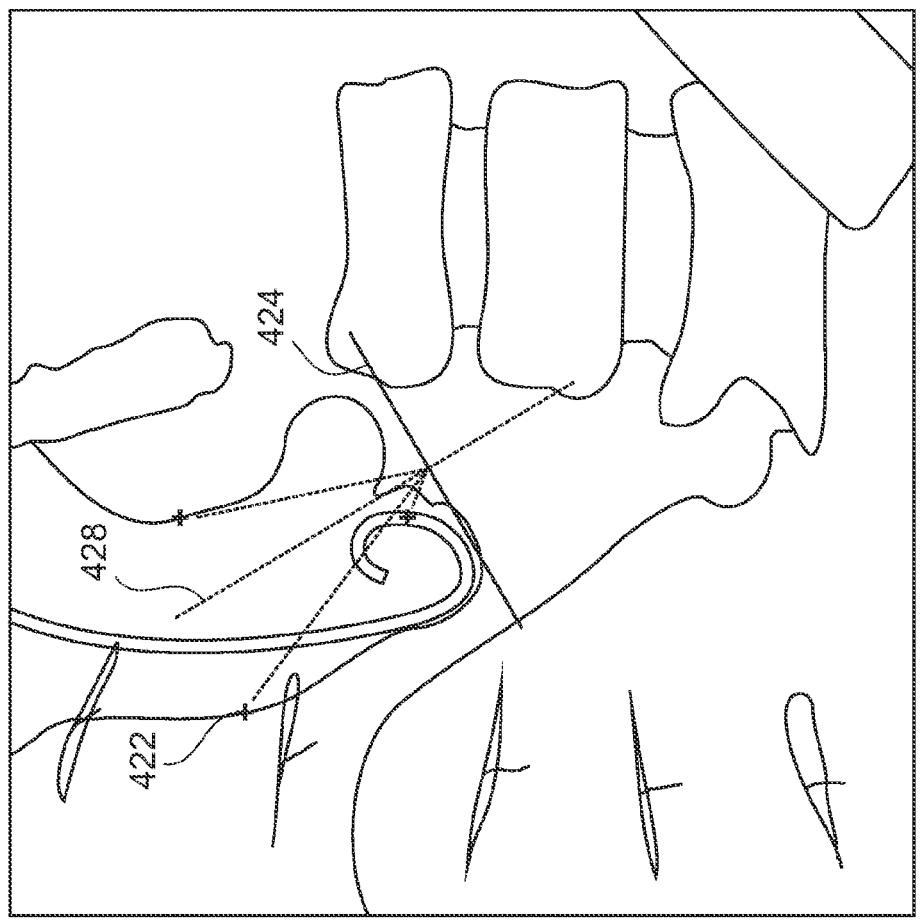
FIG. 14 shows a transform of the plane and the medial axis versus tracked calcifications.

Then, the plane 424 and the medial axis 428 are geometrically related against the aortagram-tracked calcifications, as schematically shown in FIG. 14. This defines a forward geometrical transform linking plane 424 and axis 428 to calcifications 422.

Figure 15:
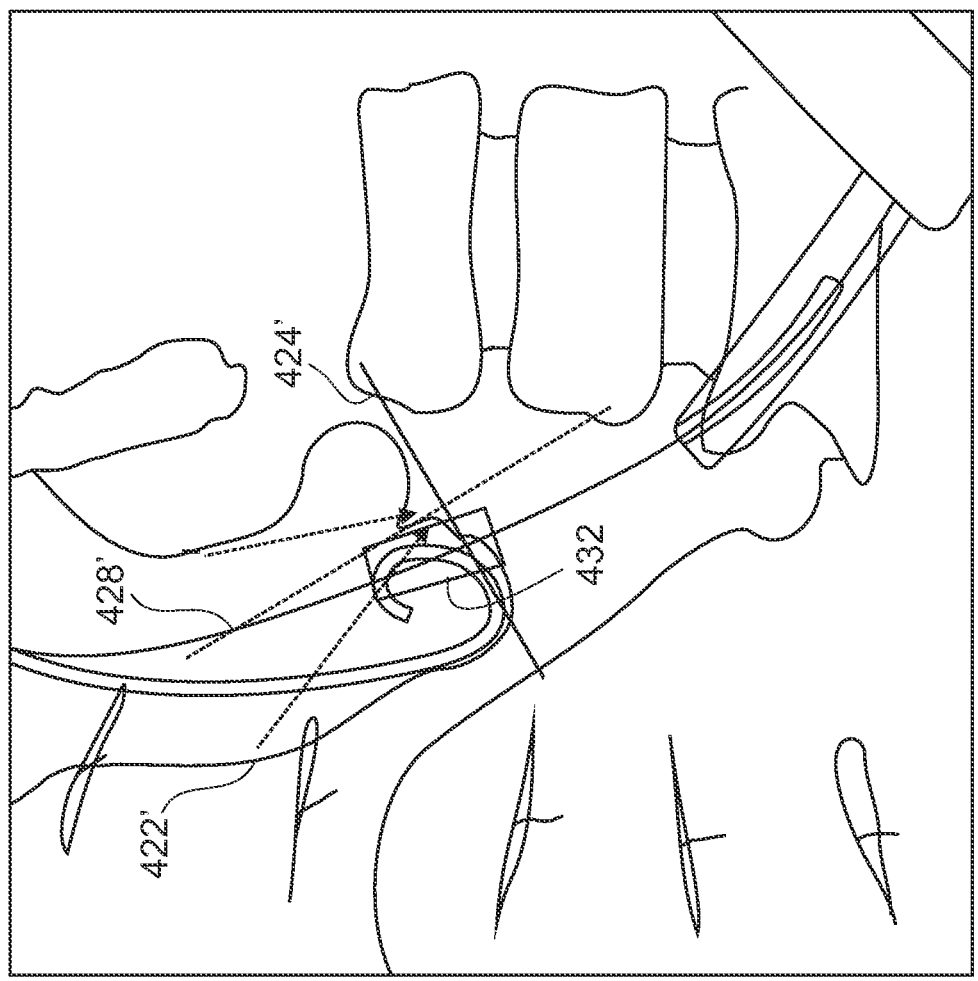
FIG. 15 shows a transformed registered plane and medial axis from a fluoro-image based on tracked calcifications.
Figure 20:
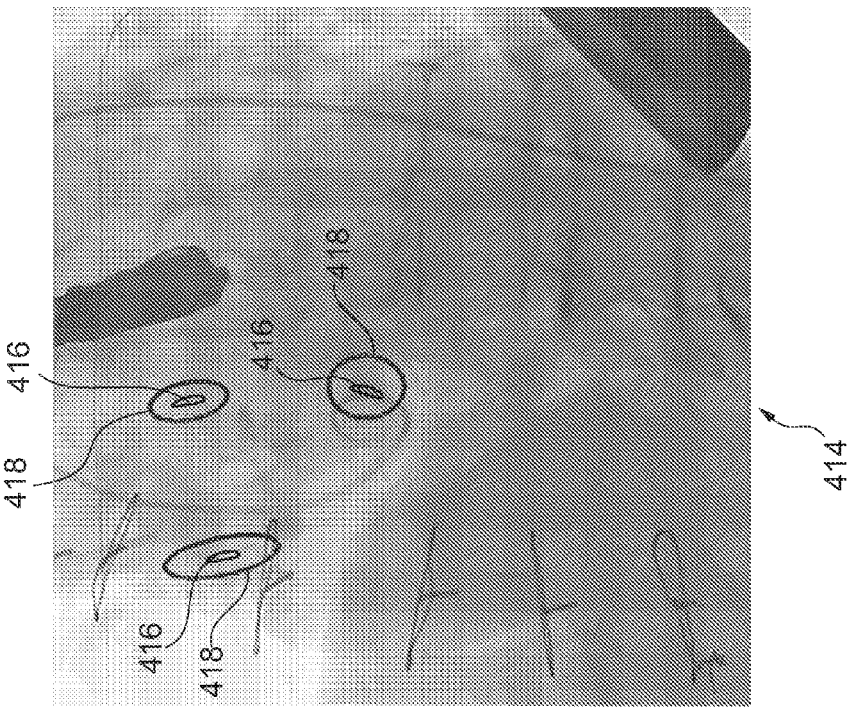
Figure 19:
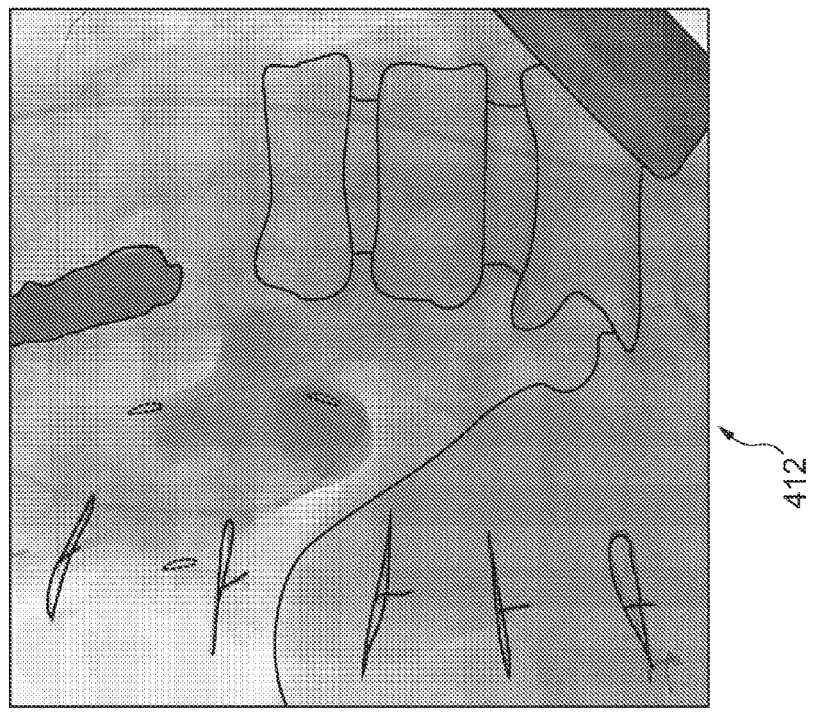
Figure 23:
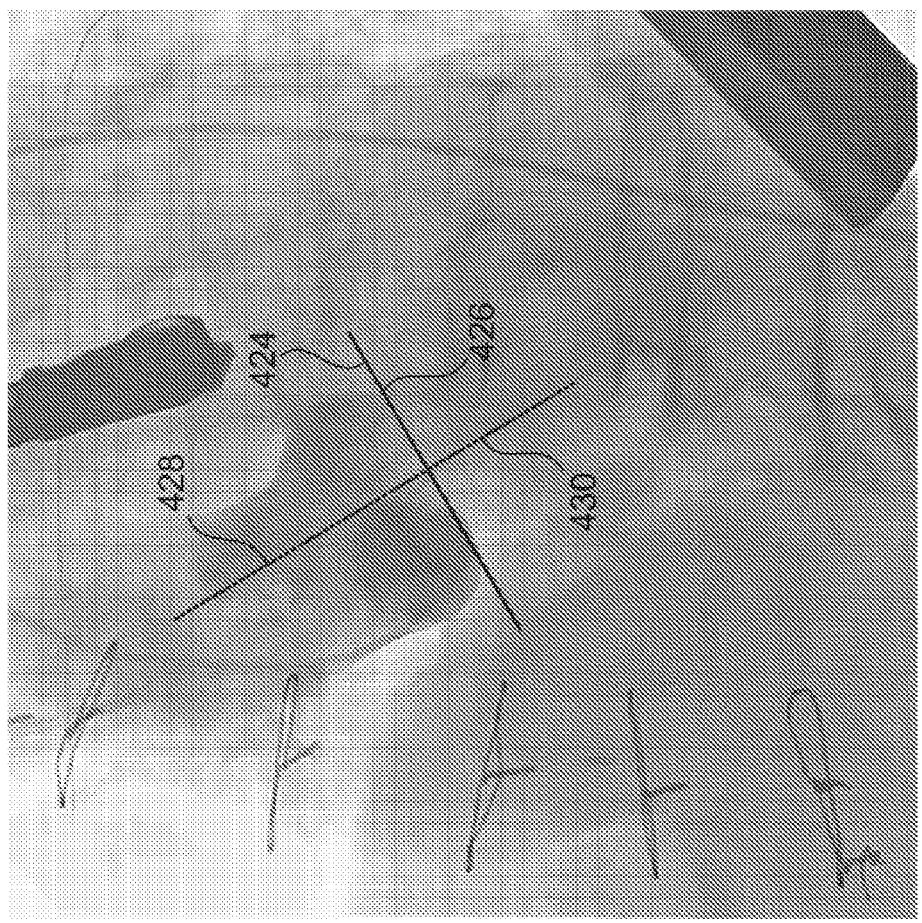
Figure 24:
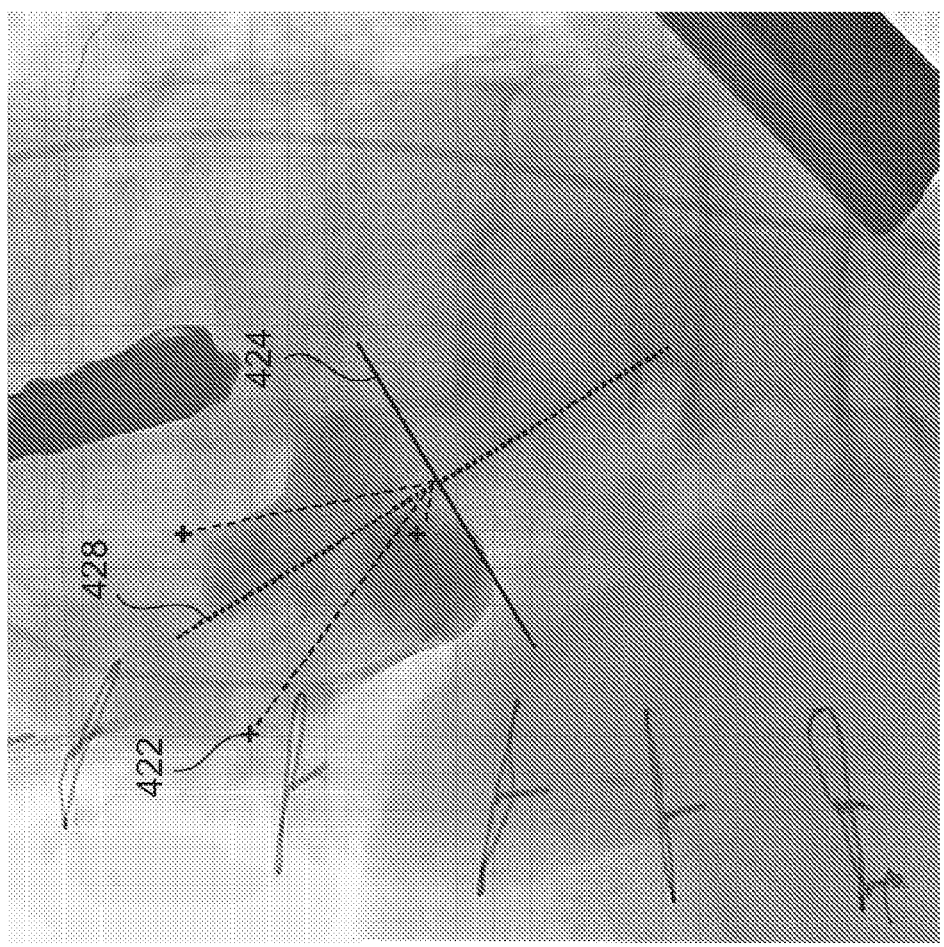
Figure 25:
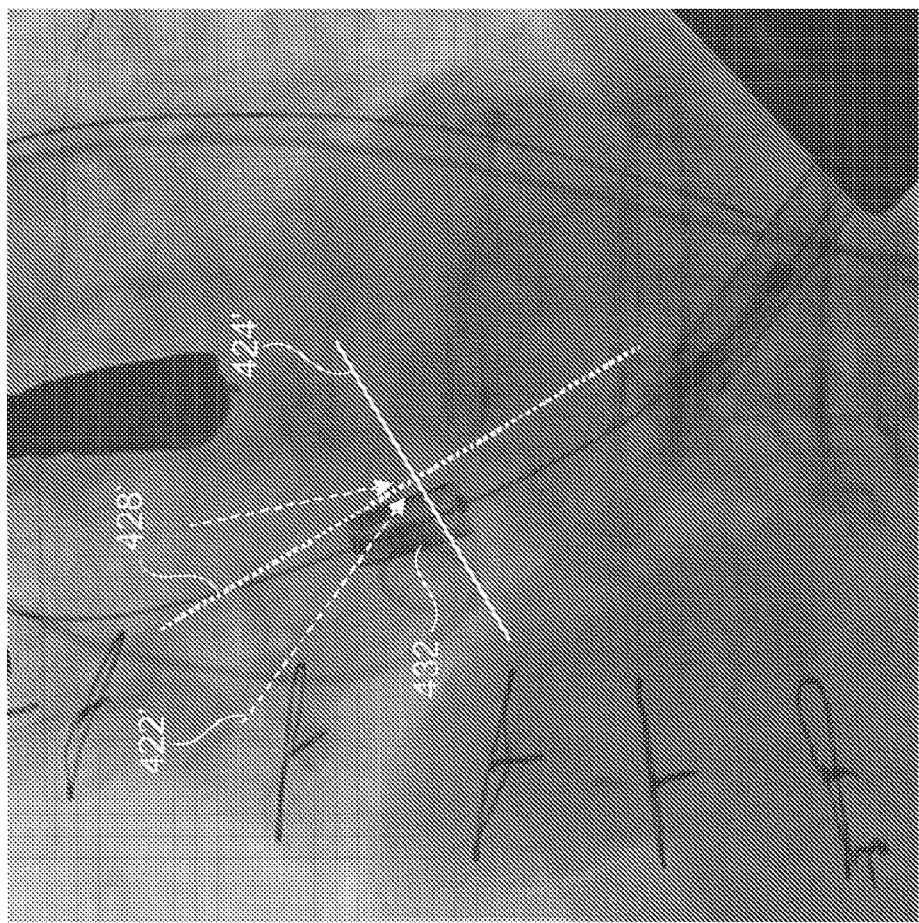

Further, FIG. 15 shows that registered plane 424' and registered medial axis 428' from tracked calcifications in the fluoro live image are also transformed according to the spatial data. This is achieved by inversing the forward geometrical transform mentioned above and by applying the resulting backward transform that links tracked calcifications 422' to the newly estimated plane 424' and axis 428'. It is noted, that FIG. 15 also shows an inserted percutaneous valve 432.

FIGS. 16 to 18 show photographic images using X-ray images in addition to the drawings of FIGS. 6 to 8, for a better understanding of the invention.

FIGS. 19 to 25 show photographic images using X-ray images in addition to the drawings of FIGS. 9 to 15, for a better understanding of the invention.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage.

A computer program may be stored and/or distributed on a suitable medium, such as an optical storage medium or a solid state medium supplied together with or as part of other hardware, but may also be distributed in other forms, such as via the internet or other wired or wireless telecommunication systems.

Any reference signs in the claims should not be construed as limiting the scope.

The invention claimed is:

1. A medical imaging arrangement for accurate positioning for vessel intervention procedures, the arrangement comprising:
   an X-ray image acquisition device;
   a data processing unit; and
   a display device;
   the data processing unit being configured for acquiring via said X-ray image acquisition device:
      a plurality of X-ray images of a vessel region of interest with injected contrast agent; and
      at least one current fluoroscopy image of the vessel region of interest; and further configured for:
      identifying vessel information data within said plurality of X-ray images;
      detecting first calcification features of a vessel in the vessel region of interest in said plurality of X-ray images;
      generating vessel representation using the vessel information data and the detected calcification features;

detecting second calcification features of the vessel in the vessel region of interest in the current fluoroscopy image, wherein the second calcification features are corresponding to the first calcification features;

registering the vessel representation with said fluoroscopy image, the calcification features being used for the registration;

generating a composite image by combining the vessel representation with said fluoroscopy image;

displaying the composite image via said display device, said acquiring of the X-ray images comprising acquiring a sequence of images, said sequence comprising multiple images of a contrast phase and multiple images of a non-contrasted phase;

tracking the images of the sequence until determining that the first calcification features have become visible in the non-contrasted phase;

locating the calcification features with respect to the vessel information data corresponding to an acquired image in the contrast phase;

recording spatial relationships linking contours discerned from said tracking; and applying the spatial relationships to the calcification features, in order to use said features in said registering.

2. The arrangement of claim 1, configured for performing, automatically and without need for user intervention, said acquiring, tracking, identifying of first and second calcification features, detecting, generating of a vessel representation and a composite image, locating, recording, applying, registering, and displaying.

3. The arrangement of claim 1, said calcification features residing on an outline of the aorta.

4. The arrangement of claim 1, the linked contours being dividable into pairs, one contour of the pair being in an image from among said multiple of said contrast phase, the other contour being in image from said multiple of said non-contrasted phase.

5. A non-transitory computer readable medium embodying a program for medical imaging in accurate positioning for vessel intervention procedures, said program having instructions executable by a processor for carrying out a plurality of acts, from among said plurality there being the acts of:

acquiring a sequence of images comprising a plurality of images wherein a vessel region of interest is, in a contrast phase, filled with injected contrast agent such that calcification features are not visible and comprising another plurality of images wherein said vessel region of interest is less filled with injected contrast agent such that the one or more of said features is visible;

tracking the images of the sequence until contrast agent starts disappearing;

identifying the calcification features once they become visible in the tracked images of the sequence;

recording spatial relationships linking contours discerned from said tracking; and applying said spatial relationships to the calcification features in a manner temporally reverse to that of said tracking, so that a vessel representation generated based on the calcification features is registrable to a fluoroscopic image of said vessel region of interest.

6. The computer readable medium according to claim 5, said acquiring of at least one X-ray image involving acquiring a sequence of images of the region of interest with injected contrast agent, the data processing unit being configured for selecting, based on optimal contrast, an image from among said sequence.

7. The computer readable medium according to claim 5, said calcification features residing on an outline of the aorta.

8. The computer readable medium according to claim 5, from among said plurality of acts, there being the further act of generating a composite image by combining the vessel representation with the fluoroscopic image, said generating the composite image comprising a geometrical transformation such as to bring a reference image into spatial correspondence with a live image.

9. The computer readable medium according to claim 5, the generating of said vessel representation using vessel information data identified within said sequence of images and comprising modeling vessel representation using the vessel information data and the detected calcification features.

10. The computer readable medium of claim 5, the generating also being based on vessel information identified within said sequence of images.

11. The computer readable medium of claim 5, the acts of acquiring, tracking, identifying, recording and applying being performed automatically and without need for user intervention.

12. A medical imaging apparatus for accurate positioning for vessel intervention procedures, said apparatus including an image acquisition device and configured for:

acquiring, via said device, a sequence of images comprising a plurality of images wherein a vessel region of interest is, in a contrast phase, filled with injected contrast agent such that calcification features are not visible and comprising another plurality of images wherein said vessel region of interest is less filled with injected contrast agent such that the one or more of said features is visible;

tracking the images of the sequence until contrast agent starts disappearing;

identifying the calcification features once they become visible in the tracked images of the sequence;

recording spatial relationships linking contours discerned from said tracking; and applying said spatial relationships to the calcification features in a manner temporally reverse to that of said tracking, so that a vessel representation generated based on the calcification features is registerable to a fluoroscopic image of said vessel region of interest.

13. An X-ray imaging system comprising an apparatus according to claim 12.

14. A catheterization laboratory system comprising an apparatus according to claim 12.

15. The apparatus of claim 12, further comprising a data processing unit configured for performing, automatically and without need for user intervention, said acquiring, tracking, identifying, recording and applying.

16. The apparatus of claim 12, further configured for selecting, based on optimal contrast, an image from among said sequence.

17. The apparatus of claim 12, said calcification features residing on an outline of the aorta.

18. The apparatus of claim 12, further configured for generating a composite image by combining the vessel representation with the fluoroscopic image, said generating the composite image comprising a geometrical transformation such as to bring a reference image into spatial correspondence with a live image.

19. The apparatus of claim 12, further configured for:

identifying vessel information data within said sequence of images, said generating of the vessel representation using the vessel information data and the detected calcification features.

20. The apparatus of claim 12, the linked contours being dividable into pairs, one contour of the pair being in an image from among said plurality of images, the other contour being in image from said multiple of said another plurality of images.

* * * * *